United States Patent [19]
Saba

[11] Patent Number: 5,649,549
[45] Date of Patent: Jul. 22, 1997

[54] CONTRACEPTIVE DEVICE FOR ORAL SEX

[76] Inventor: Gracie M. Saba, 5150 N. Valentine Ave. #203, Fresno, Calif. 93711

[21] Appl. No.: 659,287

[22] Filed: Jun. 6, 1996

[51] Int. Cl.⁶ ............................................. A61F 6/02
[52] U.S. Cl. ............................... 128/842; 128/859
[58] Field of Search .................... 128/846, 848, 128/859–862; 2/2; 433/6, 136, 137

[56] References Cited

U.S. PATENT DOCUMENTS 1,604,136  10/1926  Stoloff ................................. 433/137
3,478,432  11/1969  Gross .................................. 433/137
4,828,491  5/1989   Gray ................................... 433/136
4,949,731  8/1990   Harding ............................... 128/844
5,318,043  6/1994   Burr ................................... 128/844

*Primary Examiner*—Michael A. Brown

[57] ABSTRACT

A contraceptive device for oral sex including a body portion having a rounded upper portion, a tapered lower portion, and an intermediate portion therebetween. A plurality of nubs extend outwardly from the intermediate portion of the body portion. The body portion is securable over the genitalia area of a woman with the plurality of nubs disposed over a clitoral area of the woman to allow for safe oral stimulation thereof.

6 Claims, 3 Drawing Sheets

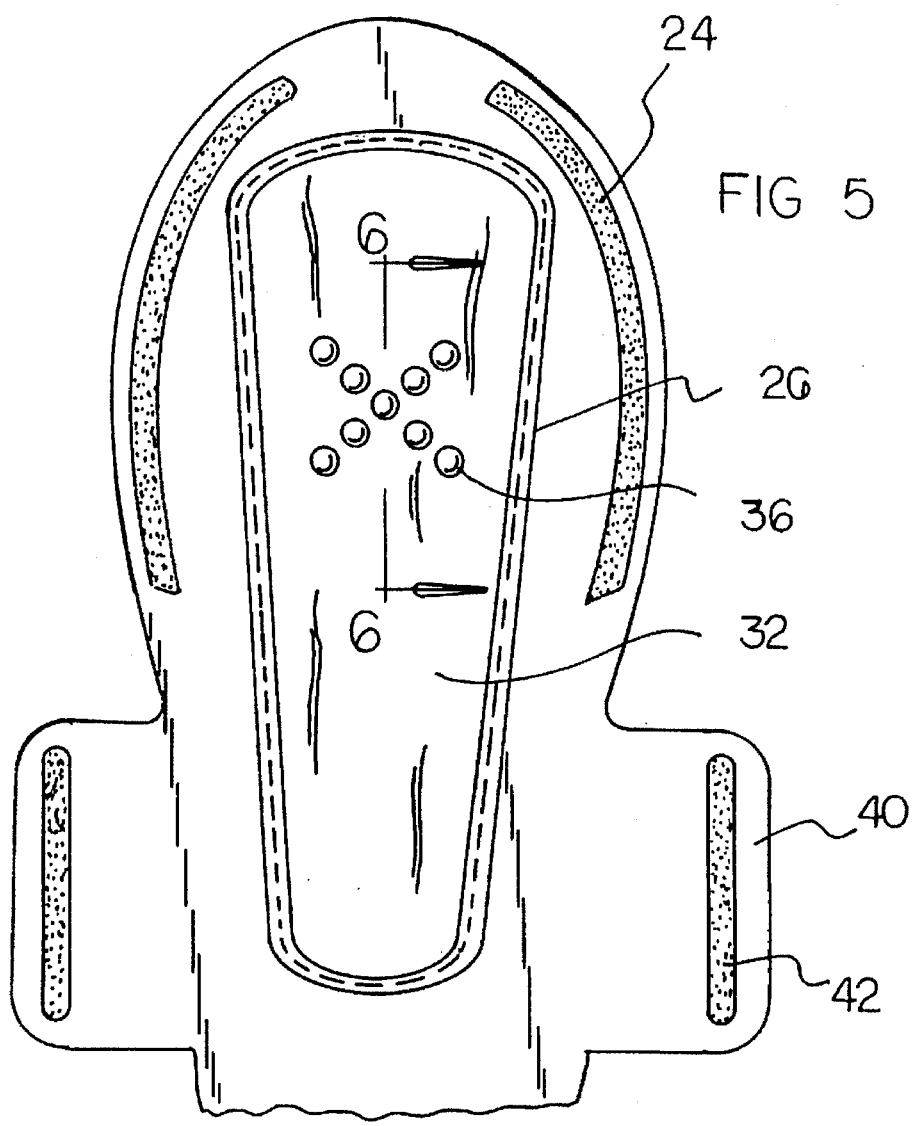
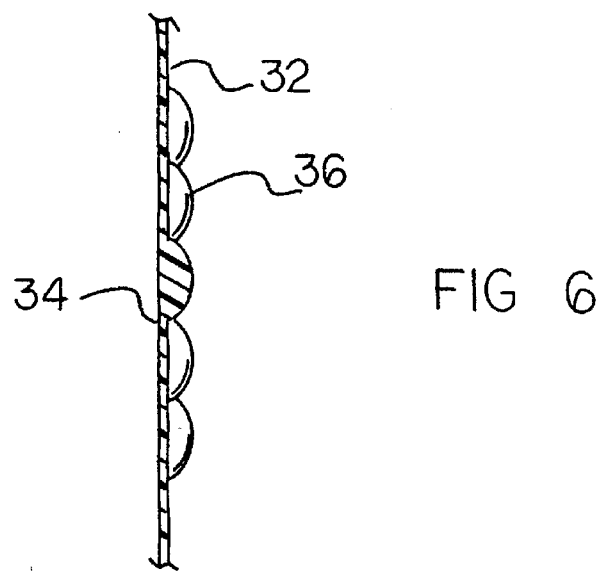

CONTRACEPTIVE DEVICE FOR ORAL SEX

BACKGROUND OF THE INVENTION

1. Field of the Invention

The present invention relates to a contraceptive device for oral sex and more particularly pertains to reducing risks of transmitting sexually transmitted diseases with a contraceptive device for oral sex.

2. Description of the Prior Art

The use of condom devices is known in the prior art. More specifically, condom devices heretofore devised and utilized for the purpose of providing sexual protection are known to consist basically of familiar, expected and obvious structural configurations, notwithstanding the myriad of designs encompassed by the crowded prior art which have been developed for the fulfillment of countless objectives and requirements.

By way of example, U.S. Pat. No. 5,390,681 to Daley discloses a prophylactic device for oral sex.

U.S. Pat. No. 4,875,490 to Quiroz discloses an intravaginal device.

U.S. Pat. No. Des. 354,346 to Brown discloses the ornamental design for an oral condom.

U.S. Pat. No. 4,840,624 to Lee discloses a female condom device.

U.S. Pat. No. 5,409,016 to Bloodshaw discloses an oral condom for preventing sexually transmitted diseases.

U.S. Pat. No. 5,181,527 to Dorsey et al. discloses a prophylactic device.

While these devices fulfill their respective, particular objective and requirements, the aforementioned patents do not describe a contraceptive device for oral sex for reducing risks of transmitting sexually transmitted diseases.

In this respect, the contraceptive device for oral sex according to the present invention substantially departs from the conventional concepts and designs of the prior art, and in doing so provides an apparatus primarily developed for the purpose of reducing risks of transmitting sexually transmitted diseases.

Therefore, it can be appreciated that there exists a continuing need for new and improved contraceptive device for oral sex which can be used for reducing risks of transmitting sexually transmitted diseases. In this regard, the present invention substantially fulfills this need.

SUMMARY OF THE INVENTION

In the view of the foregoing disadvantages inherent in the known types of condom devices now present in the prior art, the present invention provides an improved contraceptive device for oral sex. As such, the general purpose of the present invention, which will be described subsequently in greater detail, is to provide a new and improved contraceptive device for oral sex and method which has all the advantages of the prior art and none of the disadvantages.

To attain this, the present invention essentially comprises a body portion having planar interior and exterior surfaces. The body portion has a rounded upper portion, a tapered lower portion, and an intermediate portion therebetween. The rounded upper portion has a pair of adhesive strips disposed thereon on the interior surface of the body portion. The intermediate portion has an opening therein extending through the interior and exterior surfaces of the body portion. The body portion is dimensioned for covering a genitalia area of a woman. A soft layer is disposed within the opening in the intermediate portion. The soft layer has an interior surface and an exterior surface. The interior surface has a plurality of nubs extending outwardly therefrom. The plurality of nubs form an X-shaped configuration. A pair of wings extend outwardly from opposing side surfaces of the intermediate portion of the body portion. The pair of wings have adhesive disposed on an interior surface thereof.

There has thus been outlined, rather broadly, the more important features of the invention in order that the detailed description thereof that follows may be better understood, and in order that the present contribution to the art may be better appreciated. There are, of course, additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new and improved contraceptive device for oral sex which has all the advantages of the prior art condom devices and none of the disadvantages.

It is another object of the present invention to provide a new and improved contraceptive device for oral sex which may be easily and efficiently manufactured and marketed.

It is a further object of the present invention to provide a new and improved contraceptive device for oral sex which is of durable and reliable construction.

An even further object of the present invention is to provide a new and improved contraceptive device for oral sex which is susceptible of a low cost of manufacture with regard to both materials and labor, and which accordingly is then susceptible of low prices of sale to the consuming public, thereby making such a contraceptive device for oral sex economically available to the buying public.

Still yet another object of the present invention is to provide a new and improved contraceptive device for oral sex which provides in the apparatuses and methods of the prior art some of the advantages thereof, while simultaneously overcoming some of the disadvantages normally associated therewith.

Even still another object of the present invention is to provide a new and improved contraceptive device for oral sex for reducing risks of transmitting sexually transmitted diseases.

Lastly, it is an object of the present invention to provide a new and improved contraceptive device for oral sex including a body portion having a rounded upper portion, a tapered lower portion, and an intermediate portion therebetween. A plurality of nubs extend outwardly from the intermediate portion of the body portion. The body portion is securable over the genitalia area of a woman with the plurality of nubs disposed over a clitoral area of the woman to allow for safe oral stimulation thereof.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein:

FIG. 5 is a rear view of the present invention as taken along line 5—5 of FIG. 4.

FIG. 6 is a cross-sectional view as taken along line 6—6 of FIG. 5.

The same reference numerals refer to the same parts through the various Figures.

DESCRIPTION OF THE PREFERRED EMBODIMENT

Figure 1:
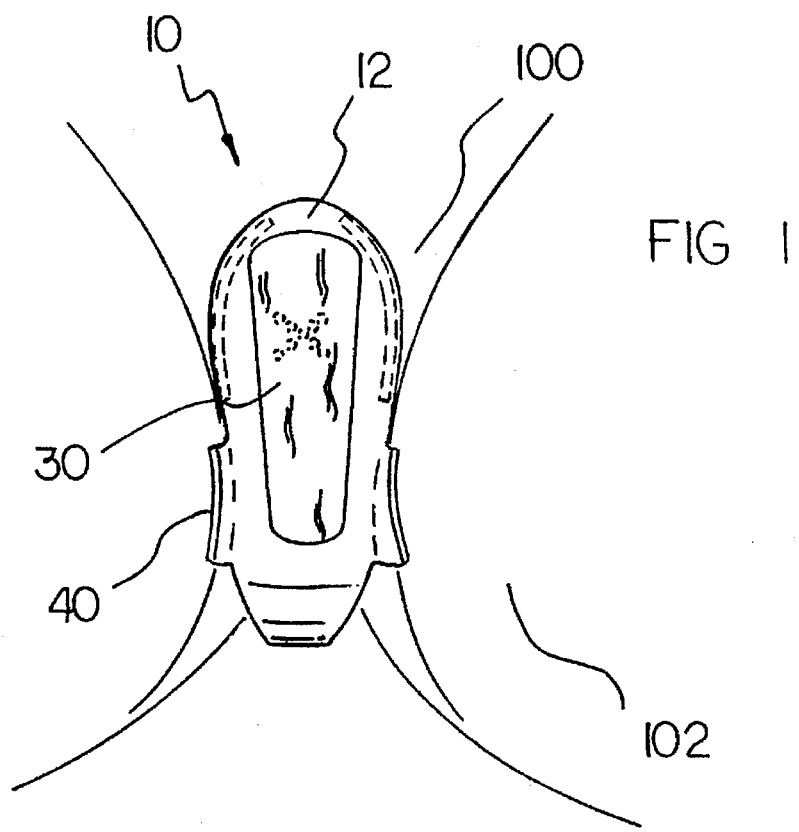
FIG. 1 is a front view of the present invention in place on a wearer.
Figure 2:
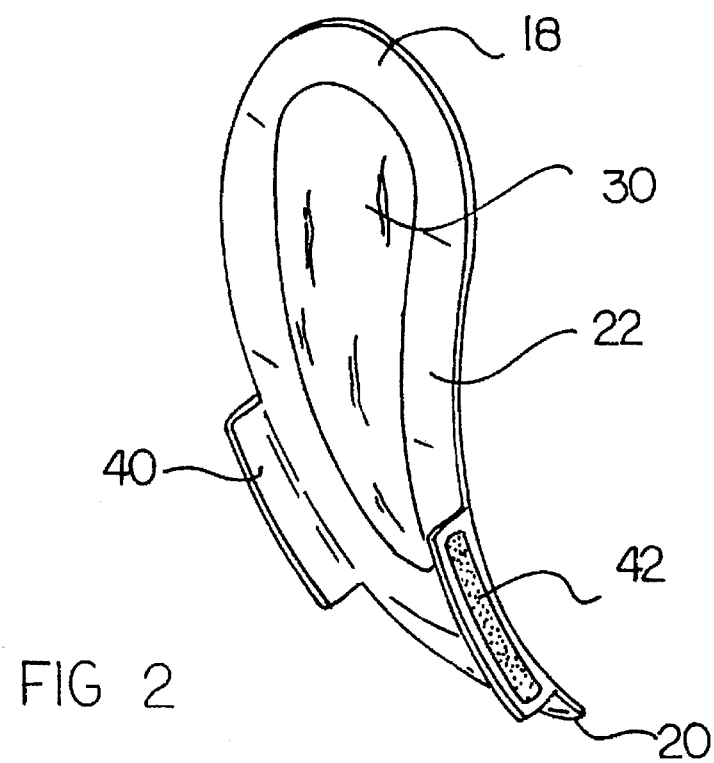
FIG. 2 is a perspective view of the preferred embodiment of the contraceptive device for oral sex constructed in accordance with the principles of the present invention.
Figure 3:
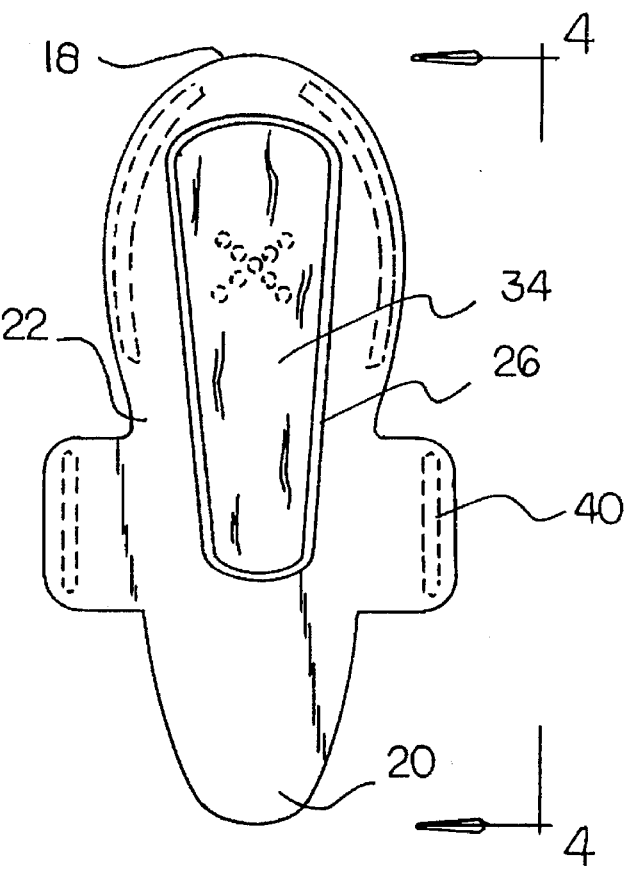
FIG. 3 is a front elevation view of the present invention.
Figure 4:
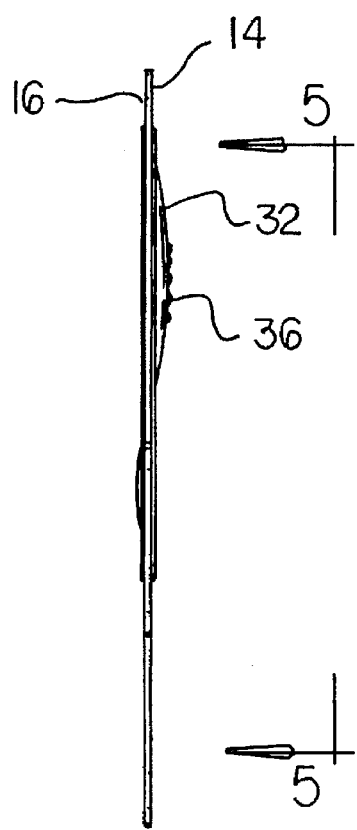
FIG. 4 is a side view of the present invention as taken along line 4—4 of FIG. 3.

With reference now to the drawings, and in particular, to FIGS. 1–6 thereof, the preferred embodiment of the new and improved contraceptive device for oral sex embodying the principles and concepts of the present invention and generally designated by the reference number 10 will be described.

Specifically, it will be noted in the various Figures that the device relates to a contraceptive device for oral sex for reducing risks of transmitting sexually transmitted diseases. In its broadest context, the device consists of a body portion, a soft layer, and a pair of wings. Such components are individually configured and correlated with respect to each other so as to attain the desired objective.

The device 10 includes a body portion 12 having planar interior 14 and exterior surfaces 16. The body portion 12 has a rounded upper portion 18, a tapered lower portion 20, and an intermediate portion 22 therebetween. The rounded upper portion 18 has a pair of adhesive strips 24 disposed thereon on the interior surface 14 of the body portion 12. The adhesive strips 24 are curved to correspond with the rounded upper portion. Note FIG. 5. The intermediate portion 22 has an opening 26 therein extending through the interior 14 and exterior surfaces 16 of the body portion 12. The body portion 12 is dimensioned for covering a genitalia area 100 of a woman. The rounded upper portion 18 extends above the genitalia area 100 to allow for the adhesive strips 24 to be safely secured to the body of the woman. The adhesive strips 24 will include a peel away layer thereover to maintain the strips 24 prior to use. The body portion 12 will be preferably fabricated of a latex material similar to materials used in the fabricated of dish gloves. The body portion 12 can be made in a variety of sizes to accommodate different sized women.

A soft layer 30 is disposed within the opening 26 in the intermediate portion 22. The soft layer 30 has an interior surface 32 and an exterior surface 34. The interior surface 32 has a plurality of nubs 36 extending outwardly therefrom. The plurality of nubs 36 form an X-shaped configuration. When the body portion 12 is in place over the genitalia area 100 of the woman, the soft layer 30 will be indirect contact with the vagina of the woman. The soft layer 30 is preferably fabricated of a soft latex material, similar to material used in the fabrication of condoms. This will provide a loose, flexible barrier to the vagina. This will allow greater freedom for a partner and a more realistic feeling for both persons. The plurality of nubs 36 will be positioned over the clitoris of the woman. The nubs 36 will serve to increase the sensation felt by the woman during oral sex.

A pair of wings 40 extend outwardly from opposing side surfaces of the intermediate portion 22 of the body portion 12. The pair of wings 40 have adhesive 42 disposed on an interior surface thereof. A peel away layer will be disposed over the adhesive 42. The pair of wings 40 extend away from the body portion 12 to adhere to legs 102 of the woman to provide greater securement of the device 10 to the woman.

As to the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and the manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modification and changes will readily occur to those skilled in the art, it is not desired to limit the invention to the exact construction and operation shown and described, and accordingly, all suitable modification and equivalents may be resorted to, falling within the scope of the invention.

What is claimed as being new and desired to be protected by LETTERS PATENT of the United States is as follows:

1. A contraceptive device for oral sex for reducing risks of transmitting sexually transmitted diseases comprising, in combination:

a body portion having planar interior and exterior surfaces, the body portion having a rounded upper portion, a tapered lower portion, and an intermediate portion therebetween, the rounded upper portion having a pair of adhesive strips disposed thereon on the interior surface of the body portion, the intermediate portion having an opening therein extending through the interior and exterior surfaces of the body portion, the body portion dimensioned for covering a genitalia area of a woman;

a soft layer disposed within the opening in the intermediate portion, the soft layer having an interior surface and an exterior surface, the interior surface having a plurality of nubs extending outwardly therefrom, the plurality of nubs forming an X-shaped configuration; and a pair of wings extending outwardly from opposing side surfaces of the intermediate portion of the body portion, the pair of wings having adhesive disposed on an interior surface thereof.

2. A contraceptive device for oral sex comprising:

a generally planar body portion having a rounded upper portion, a tapered lower portion, and an intermediate portion therebetween; and a plurality of nubs extending outwardly from the intermediate portion of the body portion.

3. The contraceptive device as set forth in claim 2 wherein the rounded upper portion having a pair of adhesive strips disposed thereon on the interior surface of the body portion.

4. The contraceptive device as set forth in claim 2 wherein a soft layer disposed within an opening in the intermediate portion of the body portion, the soft layer having an interior surface and an exterior surface, the interior surface having the plurality of nubs extending outwardly therefrom.

5. The contraceptive device as set forth in claim 4 wherein the plurality of nubs forming an X-shaped configuration.

6. The contraceptive device as set forth in claim 2 and further including a pair of wings extending outwardly from opposing side surfaces of the intermediate portion of the body portion, the pair of wings having adhesive disposed on an interior surface thereof.

* * * * *